US005876940A

United States Patent [19]
Groden et al.

[11] Patent Number: 5,876,940
[45] Date of Patent: Mar. 2, 1999

[54] ALLELES

[75] Inventors: Joanna L. Groden, Cincinnati, Ohio; Raymond L. White, Salt Lake City, Utah; Lisa Spirio, Salt Lake City, Utah; Margaret Robertson, Salt Lake City, Utah; Robert Weiss, Salt Lake City, Utah; Thérèse Tuohy, Cincinnati, Ohio

[73] Assignee: University of Utah Research Foundation, Salt Lake City, Utah

[21] Appl. No.: 867,579

[22] Filed: Jun. 2, 1997

Related U.S. Application Data

[63] Continuation of Ser. No. 351,151, Nov. 30, 1994, abandoned.
[51] Int. Cl.$^6$ ............................. C12Q 1/68; C12P 19/34
[52] U.S. Cl. ........................... 435/6; 435/91.2; 435/69.1; 435/69.7; 935/16; 935/78
[58] Field of Search .............................. 435/6, 69.1, 69.7, 435/91.2; 935/16, 78

[56] References Cited

U.S. PATENT DOCUMENTS 4,683,195  7/1987  Mullis et al. .
4,683,202  7/1987  Mullis .

OTHER PUBLICATIONS

Varesco, L. et al. (1993). "A Rapid Screening Method to Detect Nonsense and Frameshift Mutations: Identification of Disease–causing APC Alleles," *Cancer Res. 53*:5581–5584.

Harris, C.C. (1993). "p53: At the Crossroads of Molecular Carcinogenesis and Risk Assessment," *Science 262*:1980–1981.

Frebourg, T. et al. (1992). "A Functional Screen for Germ Line p53 Mutations Based on Transcriptional Activation," *Cancer Res. 52*:6976–6978.

Wu, D.Y. and Wallace, R.B. (1989). "The Ligation Amplification Reaction (LAR)—Amplification of Specific DNA Sequences Using Sequential Rounds of Template–Dependent Ligation," *Genomics 4*:560–569.

*Primary Examiner*—Carla J. Myers
*Attorney, Agent, or Firm*—Rothwell, Figg, Ernst & Kurz, P.C.

[57] ABSTRACT

The present invention relates to a functional screen assay for nonsense or frameshift mutations that allows genes of interest to be scanned. This assay is based on the cloning of segments of the gene of interest in-frame with a sequence coding for a marker followed by screening for the level of expression of the marker. Individuals at risk for any one of a number of genetic diseases, which are associated with such nonsense or frameshift mutations, can be quickly screened for chain-terminating mutations introduced by these nonsense and frameshift mutations. At present, scanning of many genes for mutations requires significant effort because the genes are large and most mutations are unique. Therefore, this assay offers a powerful option for the diagnosis of many genetic diseases.

34 Claims, 4 Drawing Sheets

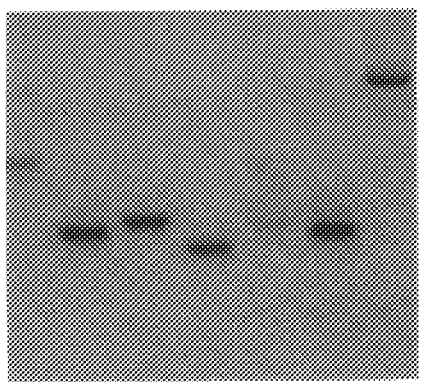
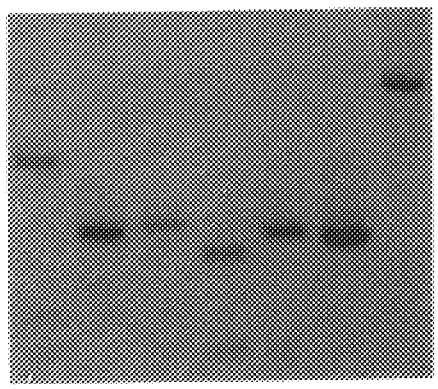
FIG. 3A
FIG. 3B

SEQUENCE LISTING ( 1 ) GENERAL INFORMATION:

( i i i ) NUMBER OF SEQUENCES: 16

( 2 ) INFORMATION FOR SEQ ID NO:1:

( i ) SEQUENCE CHARACTERISTICS:
        ( A ) LENGTH: 50 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:

(A) ORGANISM: Homo sapiens (xi) SEQUENCE DESCRIPTION: SEQ ID NO:1:

GGCTGCAGGA ATTCGATATC AAGCTTTGCT GCCCATACAC ATTCAAACAC          50

(2) INFORMATION FOR SEQ ID NO:2:

(i) SEQUENCE CHARACTERISTICS:
    (A) LENGTH: 44 base pairs
    (B) TYPE: nucleic acid
    (C) STRANDEDNESS: single
    (D) TOPOLOGY: linear (ii) MOLECULE TYPE: DNA (genomic)

(iii) HYPOTHETICAL: NO (iv) ANTI-SENSE: NO (vi) ORIGINAL SOURCE:
    (A) ORGANISM: Homo sapiens (xi) SEQUENCE DESCRIPTION: SEQ ID NO:2:

GGCTGCGGAA TTCGATATGG GCCCATGAGT GGGGTCTCCT GAAC               44

(2) INFORMATION FOR SEQ ID NO:3:

(i) SEQUENCE CHARACTERISTICS:
    (A) LENGTH: 43 base pairs
    (B) TYPE: nucleic acid
    (C) STRANDEDNESS: single
    (D) TOPOLOGY: linear (ii) MOLECULE TYPE: DNA (genomic)

(iii) HYPOTHETICAL: NO (iv) ANTI-SENSE: NO (vi) ORIGINAL SOURCE:
    (A) ORGANISM: Homo sapiens (xi) SEQUENCE DESCRIPTION: SEQ ID NO:3:

TGCCCATGGT TGTTGTATAA AAACTTGTTT CTATTTATT TAG                 43

(2) INFORMATION FOR SEQ ID NO:4:

(i) SEQUENCE CHARACTERISTICS:
    (A) LENGTH: 48 base pairs
    (B) TYPE: nucleic acid
    (C) STRANDEDNESS: single
    (D) TOPOLOGY: linear (ii) MOLECULE TYPE: cDNA (iii) HYPOTHETICAL: YES (iv) ANTI-SENSE: NO (vi) ORIGINAL SOURCE:
    (A) ORGANISM: Homo sapiens (xi) SEQUENCE DESCRIPTION: SEQ ID NO:4:

ATGGGAAACA TTGCCGTCCC TTTTTTTAAA AAAAAAAAT AGGTCATT             48

(2) INFORMATION FOR SEQ ID NO:5:

(i) SEQUENCE CHARACTERISTICS:
    (A) LENGTH: 48 base pairs
    (B) TYPE: nucleic acid
    (C) STRANDEDNESS: single
    (D) TOPOLOGY: linear (ii) MOLECULE TYPE: cDNA (iii) HYPOTHETICAL: YES (iv) ANTI-SENSE: NO (vi) ORIGINAL SOURCE:
    (A) ORGANISM: Homo sapiens (xi) SEQUENCE DESCRIPTION: SEQ ID NO:5:

TTTAAAAAAA GGGACGGCAA TGTTTCCCAT ATGAAGAAAA GTTCCCTC    48

(2) INFORMATION FOR SEQ ID NO:6:

(i) SEQUENCE CHARACTERISTICS:
        (A) LENGTH: 45 base pairs
        (B) TYPE: nucleic acid
        (C) STRANDEDNESS: single
        (D) TOPOLOGY: linear (ii) MOLECULE TYPE: cDNA (iii) HYPOTHETICAL: YES (iv) ANTI-SENSE: NO (vi) ORIGINAL SOURCE:
        (A) ORGANISM: Homo sapiens (xi) SEQUENCE DESCRIPTION: SEQ ID NO:6:

GTACAACTTA TTTGGTTGAT ACTTTTTTAT TATTTGTGGT TTAAG    45

(2) INFORMATION FOR SEQ ID NO:7:

(i) SEQUENCE CHARACTERISTICS:
        (A) LENGTH: 45 base pairs
        (B) TYPE: nucleic acid
        (C) STRANDEDNESS: single
        (D) TOPOLOGY: linear (ii) MOLECULE TYPE: cDNA (iii) HYPOTHETICAL: YES (iv) ANTI-SENSE: NO (vi) ORIGINAL SOURCE:
        (A) ORGANISM: Homo sapiens (xi) SEQUENCE DESCRIPTION: SEQ ID NO:7:

ATAAAAAAGT ATCAACCAAA TAAGTTGTAC TGCCAAGTTA CTTAC    45

(2) INFORMATION FOR SEQ ID NO:8:

(i) SEQUENCE CHARACTERISTICS:
        (A) LENGTH: 45 base pairs
        (B) TYPE: nucleic acid
        (C) STRANDEDNESS: single
        (D) TOPOLOGY: linear (ii) MOLECULE TYPE: cDNA (iii) HYPOTHETICAL: YES (iv) ANTI-SENSE: NO (vi) ORIGINAL SOURCE:
        (A) ORGANISM: Homo sapiens (xi) SEQUENCE DESCRIPTION: SEQ ID NO:8:

CTAAGTGATA AAACAAAACT AATTAGGTTT CTTGTTTTAT TTAAG    45

( 2 ) INFORMATION FOR SEQ ID NO:9:

( i ) SEQUENCE CHARACTERISTICS:
        ( A ) LENGTH: 45 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: YES ( i v ) ANTI-SENSE: NO ( v i ) ORIGINAL SOURCE:
        ( A ) ORGANISM: Homo sapiens ( x i ) SEQUENCE DESCRIPTION: SEQ ID NO:9:

AAACCTAATT AGTTTTGTTT TATCACTTAG AAACAAGTAA CTTAC    45

( 2 ) INFORMATION FOR SEQ ID NO:10:

( i ) SEQUENCE CHARACTERISTICS:
        ( A ) LENGTH: 45 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: YES ( i v ) ANTI-SENSE: NO ( v i ) ORIGINAL SOURCE:
        ( A ) ORGANISM: Homo sapiens ( x i ) SEQUENCE DESCRIPTION: SEQ ID NO:10:

TTTTGTTTG TGGGTCATGT ACTGATGTTA ACTCCATCTA AACAG    45

( 2 ) INFORMATION FOR SEQ ID NO:11:

( i ) SEQUENCE CHARACTERISTICS:
        ( A ) LENGTH: 45 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: YES ( i v ) ANTI-SENSE: NO ( v i ) ORIGINAL SOURCE:
        ( A ) ORGANISM: Homo sapiens ( x i ) SEQUENCE DESCRIPTION: SEQ ID NO:11:

TAACATCAGT ACATGACCCA CAAACAAAAA AGGGAATTTA CTAAC    45

( 2 ) INFORMATION FOR SEQ ID NO:12:

( i ) SEQUENCE CHARACTERISTICS:
        ( A ) LENGTH: 45 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: YES ( i v ) ANTI-SENSE: NO (v i) ORIGINAL SOURCE:
  (A) ORGANISM: Homo sapiens (x i) SEQUENCE DESCRIPTION: SEQ ID NO:12:

TATCATATTT TTCCACGGAC CATCTATAAT GTGCTTAATT TTCAG                    45

(2) INFORMATION FOR SEQ ID NO:13:

(i) SEQUENCE CHARACTERISTICS:
    (A) LENGTH: 45 base pairs
    (B) TYPE: nucleic acid
    (C) STRANDEDNESS: single
    (D) TOPOLOGY: linear (i i) MOLECULE TYPE: cDNA (i i i) HYPOTHETICAL: YES (i v) ANTI-SENSE: NO (v i) ORIGINAL SOURCE:
    (A) ORGANISM: Homo sapiens (x i) SEQUENCE DESCRIPTION: SEQ ID NO:13:

ATTATAGATG GTCCGTGGAA AAATATGATA AAATAATTTA TTTAC                    45

(2) INFORMATION FOR SEQ ID NO:14:

(i) SEQUENCE CHARACTERISTICS:
    (A) LENGTH: 45 base pairs
    (B) TYPE: nucleic acid
    (C) STRANDEDNESS: single
    (D) TOPOLOGY: linear (i i) MOLECULE TYPE: cDNA (i i i) HYPOTHETICAL: YES (i v) ANTI-SENSE: NO (v i) ORIGINAL SOURCE:
    (A) ORGANISM: Homo sapiens (x i) SEQUENCE DESCRIPTION: SEQ ID NO:14:

CAAACCCTGG TCACTATTTT GTTTCTAAAC TCATTGGCC CACAG                     45

(2) INFORMATION FOR SEQ ID NO:15:

(i) SEQUENCE CHARACTERISTICS:
    (A) LENGTH: 45 base pairs
    (B) TYPE: nucleic acid
    (C) STRANDEDNESS: single
    (D) TOPOLOGY: linear (i i) MOLECULE TYPE: cDNA (i i i) HYPOTHETICAL: YES (i v) ANTI-SENSE: NO (v i) ORIGINAL SOURCE:
    (A) ORGANISM: Homo sapiens (x i) SEQUENCE DESCRIPTION: SEQ ID NO:15:

GTTTAGAAAC AAAATAGTGA CCAGGGTTTG TAATCTTCTG TTGAC                    45

(2) INFORMATION FOR SEQ ID NO:16:

(i) SEQUENCE CHARACTERISTICS:
    (A) LENGTH: 32 base pairs
    (B) TYPE: nucleic acid

```
    ( C ) STRANDEDNESS: single
    ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Homo sapiens ( x i ) SEQUENCE DESCRIPTION: SEQ ID NO:16:

TACGGGGCCC ATGTACACTA TAGAGAACAT AC                                                32
```

ALLELES

This application is a continuation of application Ser. No. 08/351,151, filed Nov. 30, 1994 now abandoned.

This invention was made with support of Grant No. 5P30-HG00199-03 awarded by the National Institutes of Health, Bethesda, Md. The government has certain rights in the invention.

BACKGROUND OF THE INVENTION

The present invention relates to a functional screen assay for nonsense or frameshift mutations that allows genes of interest to be scanned. More specifically, this invention relates to an assay for the rapid screening for a number of genetic diseases which involves the cloning of segments of a gene in-frame with a sequence coding for a marker and determining the expression level of the marker.

The publications and other materials used herein to illuminate the background of the invention, and in particular cases to provide additional details respecting the practice of the invention, are incorporated by reference. For convenience, the references are referenced numerically in the following text and grouped respectively in the appended bibliography.

The accurate detection of mutation in human genes is important for the clinical diagnosis of inherited diseases and diagnosis of predisposition to neoplasia. Linkage analysis can follow the inheritance of these mutant genes within kindreds with a calculated likelihood for carrier status, but only a direct analysis of the gene will determine the genotype of an at-risk individual in the absence of familial analysis. Therefore, there is a need for rapid and reliable methods for detecting mutations in human genes, especially in human tumor suppressor genes.

One human suppressor gene that represents an excellent candidate for rapid detection of mutations is adenomatous polyposis coli (APC). APC is an inherited syndrome that predispose affected individuals to colon cancer and other types of neoplasia. APC is transmitted in families as an autosomal dominant disease and is caused by mutations in the APC gene. Disruption of the APC gene leads to a highly penetrant, inherited form of colon cancer.

The distribution of germline mutations in APC has been particularly revealing. A number of different research groups have identified disease-causing germline mutations in APC. Results of most of these efforts have been summarized by Burt and Groden (1). All mutations identified to date, with the exception of five missense mutations (one of which does not segregate with the disease), are chain-terminating alterations, such as frameshifts and premature termination codons; most of these mutations are unique. Germline mutations have been detected throughout the coding elements of the gene, with some notable exceptions: no mutations have been detected in exons 1 or 2, nor, as yet, in any of the four recently identified exons upstream of exon 1; nor have any mutations been detected in a large segment of exon 15 from nucleotides 4791 to 7932, which suggests that mutations in these regions might be innocuous or lethal.

Mutational analyses of colorectal adenomas and carcinomas at the APC locus have shown that most, if not all, tumors carry at least one nonsense or frameshift APC mutation. (2–5) Many of the tumors analyzed carry two APC mutations or show a loss of heterozygosity affecting the APC region of chromosome 5. These same mutational analyses of tumors also have suggested that over 70% of APC mutations occur within a 3-kb region of exon 15. The fact that this region is contained within the 6.5-kb contiguous genomic sequence of open reading frame suggests that it may be possible to use genomic DNA as a PCR template in an assay. The majority of these mutations are unique within a given family, with the exception of two deletions that together represent about 10% of known germline mutations. Because the APC coding sequence is greater than 8.5-kb, it is extremely difficult to scan or sequence this gene rapidly.

Conventional methods of mutation screening, such as single strand conformation polymorphism analysis, denaturing-gradient gel electrophoresis, temperature-gradient gel electrophoresis, direct sequencing, or RNase protection assays, are all labor-intensive, gel-based assays that are normally reliable for DNA segments no longer than about 500 nucleotides. Other methods that are not gel-based, such as allele-specific PCR and the oligo-ligation assay, are directed only toward the identification of known mutations and are not applicable for detection of unknown mutations. These conventional methods to detect gene mutations rely either on the preparation of cDNA or on screening of each exon of a gene individually. For genes that have several exons, often spread over large distances in genomic DNA, preparation of cDNA or fragments of each individual exon can be tedious and add precious time to otherwise rapid screening processes.

However, these prior art methods are not suitable for many human disease genes. In APC screening, for example, these methods would be inefficient because none of the mutations identified to date has been found at a frequency of more than one in ten. APC is a large gene, containing over 8.5 kb of known open reading frame sequence and encoding RNAs over 10 kb in size. It is composed of at least 19 exons, some of which are alternatively spliced.

A functional assay for the detection of p53 mutations in Li-Fraumeni patients has been described in Frebourg et al. (6). In this case, however, it is the function of the gene product itself that is assayed and thus not generally applicable. The p53 gene is a human tumor suppressor gene and mutations in this gene are common in human cancer. As described by Harris (7), p53 mutations are different from those in most other tumor suppressors. For example, Harris describes that the tumor suppressor genes defective in retinoblastoma and adenomatous polyposis coli (APC) are commonly inactivated by nonsense mutations that cause truncation or instability of the protein. But Harris describes that in p53 nearly 90 percent of the mutations are missense mutations that change the identity of an amino acid in the protein.

Thus, there is a need for a rapid assay for nonsense and frameshift mutations in the diagnosis of genetic diseases. The assay of this invention allows rapid detection of mutations in genes of individuals and avoids problems with prior screening methods. The present assay is based on the level of expression of a marker, the coding sequence of which has been joined in-frame to the 3' end of an amplified and cloned DNA segment of the gene of interest.

SUMMARY OF THE INVENTION

The present invention relates to a functional screen assay for nonsense and frameshift mutations that allows genes of interest to be scanned rapidly.

It is an object of this invention to provide an assay for the rapid screening for a number of genetic diseases, which are associated with nonsense and frameshift mutations. Such diseases include APC and retinoblastoma.

It is another object of this invention to permit the rapid screening of large genes containing many exons.

The present invention relates to a functional screen assay for nonsense or frameshift mutations that allows genes of interest to be scanned. This assay is based on the cloning of segments of the gene of interest (a first DNA sequence) in-frame with a sequence coding for a marker (a second DNA sequence) followed by screening for the level of expression of the marker. Individuals at risk, for any one of a number of genetic diseases, which are associated with such nonsense or frameshift mutations, can be quickly screened for chain-terminating mutations introduced by these nonsense and frameshift mutations. At present, scanning of many genes for mutations requires significant effort because the genes are large and most mutations are unique. Therefore, this assay offers a powerful option for the diagnosis of many genetic diseases.

In one embodiment, each exon of the gene is separately amplified and combined with a marker DNA sequence. This embodiment allows rapid screening of each exon and is useful in those instances where a majority of mutations occur in one or two exons. In a second embodiment, several exons are amplified in order to concatenate exons and skip large stretches of intron sequence. By using total genomic DNA, this development avoids the need for preparation of cDNA for mutational analyses. The method may be adapted to concatenate consecutive or non-consecutive exons, allowing different (known or theoretical) splice forms of a cDNA to be amplified. This embodiment allows rapid screening of several short exons at once, rather than each exon individually. The present invention provides an assay which offers a powerful option for the diagnosis of genetic diseases which are associated with large genes generally containing multiple exons.

BRIEF DESCRIPTION OF THE FIGURES

The file of this patent contains at least one drawing executed in color. Copies of this patent with color drawings will be provided by the Patent and Trademark Office upon request and payment of the necessary fee.

FIG. 3A shows the PCR amplification of exons 3–9 of the APC gene using 10 mM Tris-HCl, 50 mM KCl, 1.5 mM $MgCl_2$, pH 8.3 at 20° C. using genomic template for exons 3–6 and 9. FIG. 3B shows the PCR amplification of exons 3–9 of the APC gene using 10 mM Tris-HCl, 50 mM KCl, 4.5 mM $MgCl_2$, pH 8.3 at 20° C. using genomic template for exons 3–6 and 9.

DETAILED DESCRIPTION OF THE INVENTION

Figure 1:
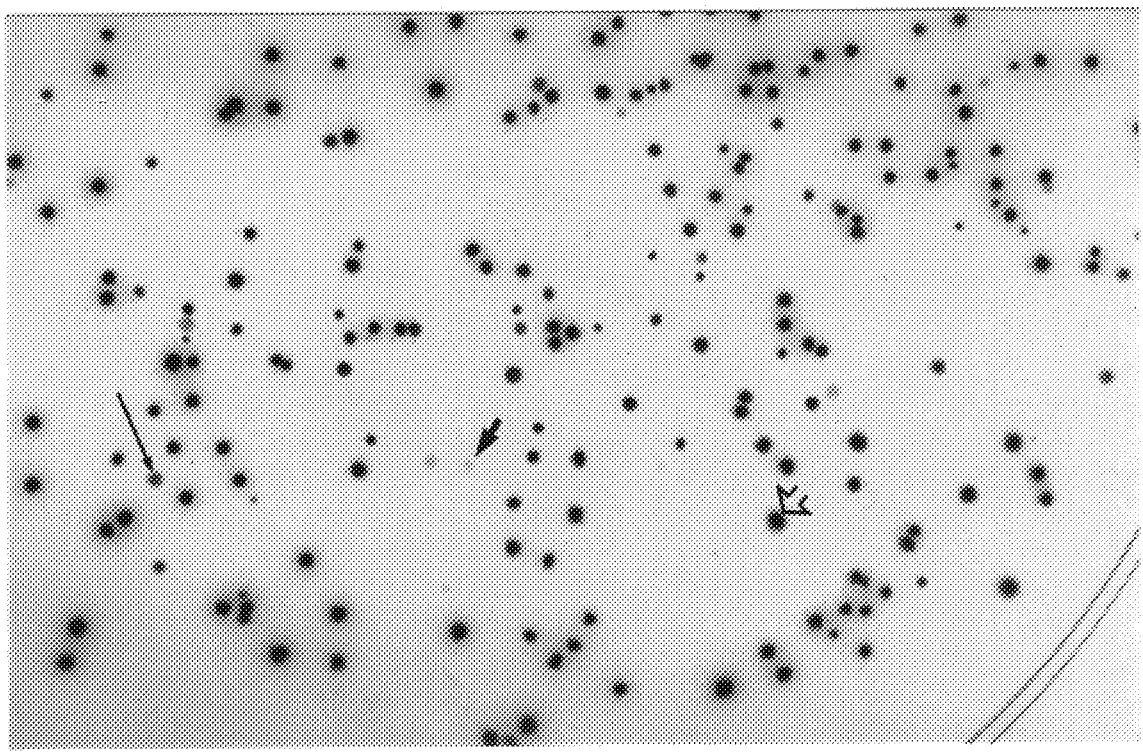
FIG. 1 shows three types of colonies that result from cloning an APC segment amplified from the DNA of a normal individual. The clear arrow points to a blue colony (in-frame cloning); the short black arrow points to a white colony (vector background); the long black arrow points to a light blue colony (translational restart of in-frame cloning or PCR error that changed the frame).

The present invention relates to a functional screen assay for nonsense or frameshift mutations that allows genes of interest to be scanned. This assay is based on the cloning of segments, preferably prepared by amplification, of the gene of interest (a first DNA sequence) in-frame with a sequence coding for a marker (a second DNA sequence, sometimes referred to as a marker DNA sequence) followed by screening for the level of expression of the marker. Individuals at risk for any one of a number of genetic diseases, which are associated with such nonsense or frameshift mutations, can be quickly screened for chain-terminating mutations introduced by these nonsense and frameshift mutations. At present, scanning of many genes for mutations requires significant effort because the genes are large and most mutations are unique. Therefore, this assay offers a powerful option for the diagnosis of many genetic diseases.

In one embodiment, each exon of the gene is separately amplified and combined with a marker DNA sequence. This embodiment allows rapid screening of each exon and is useful in those instances where a majority of mutations occur in one or two exons. In a second embodiment, several exons are amplified in order to concatenate exons and skip large stretches of intron sequence. By using total genomic DNA, this development avoids the need for preparation of cDNA for mutational analyses. The method may be adapted to concatenate consecutive or non-consecutive exons, allowing different (known or theoretical) splice forms of a cDNA to be amplified. This embodiment allows rapid screening of several short exons at once, rather than each exon individually. The present invention provides an assay which offers a powerful option for the diagnosis of genetic diseases which are associated with large genes generally containing multiple exons.

The present invention detects mutations in disease genes resulting from frameshift or nonsense mutations. Examples of the genes of interest include human tumor suppressor genes. Examples of human tumor suppression genes include APC and retinoblastoma. Detection of the mutations is accomplished by a rapid assay using a marker which is easily detected, such as colorimetric markers, immunological markers and the like. A functional assay has been designed to detect mutations that disrupt translation of the reading frame of the gene associated with a genetic disease. The assay comprises several steps: (a) amplifying a DNA sequence to provide a first DNA sequence; (b) combining the first DNA sequence upstream and in-frame with second DNA sequence for a marker; and (c) detecting the level of expression of the marker.

Many techniques for amplifying a DNA sequence are known in the art and will be useful with this invention, including a polymerase chain reaction (8), a ligase chain reaction (9) or a lexon creating reaction described infra. The specific techniques to be used will be selected as a matter of choice depending on the size of the DNA to be amplified, the number of exons to be amplified and the like in view of the parameters described herein.

Many second DNA sequences useful as markers will also be apparent to those skilled in the art, including sequences that code for an enzyme or an epitope. Moreover, when the marker is an enzyme, those skilled in the art will further recognize that various types of enzymes will be useful such as chromogenic and fluorogenic enzymes, i.e., enzymes which are capable of using chromogenic or fluorogenic substrates. A particularly well-suited enzyme is β-galactosidase. When the marker is an epitope, those skilled in the art will recognize that various epitopes, including peptide or olionucleotide epitopes, will be useful and will be detected by the appropriate polyclonal or monoclonal antibody.

Various detecting means are also known including immunological methods (e.g., ELISA), photometric methods, spectrophotometric methods, fluorometric methods, radiometric methods or visual inspections. Of course, the detection of the marker will depend upon the type of marker being used.

The amplified DNA of the gene of interest is combined with the DNA sequence for the marker in such a manner that the amplified DNA is upstream of the marker sequence and is in the proper reading frame with the marker sequence. In this manner, a nonsense or frameshift mutation will be evident by a reduced or lack of expression of the marker. Conventional techniques for combining the amplified DNA and marker DNA sequence are used. Appropriate vectors are chosen to allow the cloning of the DNA for production of the marker.

The size of a fragment that can be screened depends upon a combination of the ability of the amplification method to generate larger fragments of DNA and the ability of the marker sequence to be expressed and to function appropriately with a second, uncharacterized protein domain attached. For example, it is known that β-galactosidase can be expressed as part of a fusion protein and retain enzymatic activity. Although the function of β-galactosidase is not usually affected by the gene product attached, factors as solubility, toxicity or stability of the chimeric protein could be important. When β-galactosidase is used as the marker, the omission of isopropylthiogalactosidase (IPTG) from the plating steps of the examples of this assay was indicated by initial experiments suggesting that overexpression of the cloned gene product, when induced by IPTG, resulted in small, slow-growing colonies. This observation implies toxicity either from the high expression of the chimeric protein or from the vector in the Sure™ strain of bacteria.

The present assay will be described with reference to APC as the gene of interest and β-galactosidase as the marker. It is understood that the invention is not limited to this gene and this marker. The genomic structure of the APC gene is unusual, in that one of its exons is 6.5 kb. This size permits the majority of the open reading frame to be screened using genomic DNA. Moreover, the majority of germline mutations identified to date have occurred in this exon. The remainder of the gene is composed of at least 19 exons that are alternatively spliced. Therefore, the remainder of the open reading frame will be screened most effectively through cDNA or the PCR method of amalgamating exons that is discussed infra. This can be accomplished with one or two sets of primers, depending on the splice forms that are targeted for analysis. Most human disease genes that are candidates for screening with the method reported here, i.e., those known to carry a significant proportion of nonsense or frameshift mutations, will likewise be screened most efficiently by using cDNA or the PCR method of amalgamating exons that is discussed infra.

Three types of bacterial colonies were seen with this assay using β-galactosidase, as shown in FIG. 1. An intense blue colony was produced from in-frame cloning and maintenance of the reading frame in DNA that has a normal APC sequence. The intense blue colony results from the production of high levels of functional β-galactosidase protein. A white colony was produced by plasmid not carrying a cloned DNA insert, resulting in almost no production of β-galactosidase. The in-frame cloning of an insert that contained a sequence with a frameshift or a premature stop codon, however, produced a colony of intermediate blue color whose intensity varied with the specific mutation. The variable intensity may be due to reinitiation at downstream in-frame ATGs in the cloned APC segment (positions 2845, 2935, 3631 and 4150) or to factors specific to the plasmid and bacterial strains used in this assay.

The intermediate blue colonies derived from two types of inserts: mutations present in the original template DNA and errors generated by PCR amplification of the insert. This conclusion was supported by sequencing of dark and intermediate blue colonies derived from the testing of APC patient 3400. Each of three intermediate blue colonies sequenced contained the stop mutation found in this patient and each of three dark blue colonies contained normal APC sequence. However, four percent of colonies derived from DNA of a normal subject also were intermediate blue, implying that mutations were also present in these inserts, most likely generated by PCR.

In some platings, the intensity of the blue color obtained from normal DNA inserts may vary, especially in comparison to the lighter blue color obtained from the mutant inserts. Although it was not difficult to differentiate colors among colonies on a single plate, comparisons from one plate to another could be difficult to interpret. Colors obtained from samples with frameshifts in APC showed clear differences between the blue and the intermediate blue colonies. Colors obtained from samples with premature stop codons, however, gave a less obvious, although still distinguishable, difference in color. The type of stop codon present also slightly affected the colony colors obtained: ochres (UAG) gave a clearer difference in the two colony colors than did amber (UAA) codons. This observation reflects the ability of bacteria in general to read through some stop codons more efficiently than others. In general, ochre codons can be read through more efficiently than amber codons, although in this instance, this ability is tempered by the supE44 genotype of the Sure™ strain. The Sure™ strain of bacteria generated clearer results than either su1675 or HB101, which do not have the supE44 mutation. This gene is a nonsense suppressor that allows for about 10–20% of ambers to be read as glutamines. UGA is the least efficient of the termination codons. Other bacterial strains with different genotypes, i.e., having different attributes for reading through termination codons, will optimize color differences.

The previously described system is especially useful for determining the presence of germline mutations because the number of blue to light blue colonies is around 50%. However in detecting somatic mutations, such as in tumors or stool samples, the cancerous cells are mixed in with normal cells, and the ratio of these two cell types may be very far from 50:50. Therefore, it is preferred to enrich the assay for growth of colonies with the mutant insert. This is accomplished by eliminating or poisoning the bacterial colonies with wild-type inserts, while allowing cells with mutant inserts and hence low β-galactosidase production to survive. In the galE⁻ strain of bacteria, cells producing the wild-type level of lacZ are selected against, while colonies grow with inserts carrying gene, such as APC, mutations upstream of lacZ.

Functional β-galactosidase, while not inherently lethal, will metabolize phenylgalactoside to phenol and galactose, both of which are toxic in galE⁻ strains of *E. coli*. This double insult suffered by the galE⁻ mutant provides better selection than the effect of phenol alone on a galE⁺ strain. Therefore, if sufficient full-length β-galactosidase is produced (e.g., from a wild-type APC insert into a lacZ gene), the host will die when placed on enriched minimal media, even when supplemented with an alternative carbon source. In contrast, if sufficient full-length β-galactosidase is not produced, due to a translationally impaired insertion into the lacZ gene, the host cell will live by metabolizing the alternative carbon source. By titrating the concentration of phenylgalactoside in the medium, it is possible to adjust the assay for sensitivity to the catabolites due to low-level or background levels of β-galactosidase. The ability of glucose to partially rescue the galE⁻ mutation is also used to optimize the balance of recovery of mutations in APC with the lethality of the selection. In this way, only out-of-frame or sense-to-nonsense mutant alleles of APC will be detected, while in-frame, or normal, clones will not survive the selection.

In addition, a PCR-based method of amalgamating multiple exons into a single PCR product which then can be screened for mutation using the above described method has been developed. This method of exon-linking by PCR generates an artificial "cDNA" from several contiguous (or non-contiguous) exons, to form a single "lexon". (A lexon may be defined as an in-frame concatenation of a number of exons to form a single, continuously translatable open reading frame.)

This PCR method of forming lexons is particularly useful for the analysis of genes with many, distantly spaced exons. The method only requires knowledge of the normal framing of the exons and the sequence of the intron-exon boundaries. As illustrated below in Example 3, to concatenate two exons, 4 primers are needed; two "outside" primers corresponding to the sequences upstream of the proximal exon and downstream of the distal exon, and two "internal", mutually complementary primers, corresponding to a fusion of the intron sequences immediately 3' to the proximal exon and immediately 5' to the distal exon. Each internal primer is therefore about 40 nucleotides long, consisting of ~20 nucleotides of "upstream" and ~20 nucleotides of "downstream" intron sequence. By using the appropriate internal primer with each external primer, PCR would be expected to generate two fragments which overlap for the 40 nucleotides of internal primer sequence. A second round of PCR, which uses the products of the first round PCRs as template with the external primers, would result in the concatenation of the two smaller products to a product equal to the sum of the smaller products and the extra ~40, primer-derived nucleotides.

To drive the reaction in the desired direction and avoid mispriming to sequences complementary to the 5' ends of the primers rather than the 3' ends, a modification of the original method was incorporated. Therefore, primers of ~30 nucleotides, which were shorter at the 5' ends, and still generated primary PCR products with shared ~20 nucleotides of homology at the internal overlap were tested and found to work.

Initial experimentation demonstrated that because of the variable, and generally high AT content of intron sequences, as well as the presence of in-frame termination codons which required nucleotide substitutions to be made in the primers, several had to be unusually long to effect efficient production of specific PCR products. Because of the design of the technique, this required that almost all primers were made to the same specifications. In order to maintain the translational frame and a continuous stretch of complementarity between primers made to opposite strands of the template at the same location, pairs of primers had to be compatible. In practice this required all the primers to be replaced by longer versions of the originals. In general, the "formula" was a total of 45 nucleotides per primer; 30 at the 3' end, complementary to the sequence immediately upstream of the exon to be amplified (apart from substitutions to avoid in-frame termination codons), and 15 at the 5' end, complementary to the sequence beginning 15 nucleotides downstream of the previous exon.

The production of colonies from PCR and cloning reactions using cDNA as a template allows the opportunity to measure the relative expression level of each APC allele from each individual, as PCR would generate products in a ratio reflecting the relative amounts of APC message. This can be accomplished by making use of a nucleotide polymorphism in exon 11 of APC, resulting in the presence or absence of an RsaI restriction site at nucleotide 1458 in the APC gene. In individuals who are informative for this restriction site polymorphism, we can compare the ratio of expression from each APC allele can be compared by picking 30 colonies into water, isolating DNA by a rapid boil, using PCR to amplify this region, and cutting with RsaI. This protocol will allow a score for each colony for the presence/absence of the 1458 restriction site. The expression ratio of the two alleles can also be correlated with the clinical presentation of each patient, in order to test the hypothesis that it is the level of aberrant APC expression that coordinates with the occurrence of extracolonic manifestations of the disease.

EXAMPLES

The present invention is described by reference to the following Examples, which are offered by way of illustration and are not intended to limit the invention in any manner. Standard techniques well known in the art or techniques specifically described below were used.

Example 1

Materials and Methods

A. DNA Materials

Figure 2A:
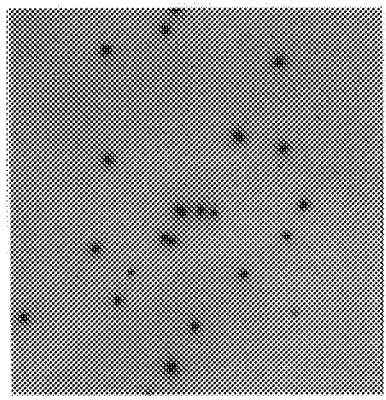
FIG. 2A shows colors and distribution of colonies containing amplified DNA from an individual with a normal genotype at the APC locus. This sample is represented numerically in Table 1 with the samples in FIG. 2B and FIG. 2C.
Figure 2B:
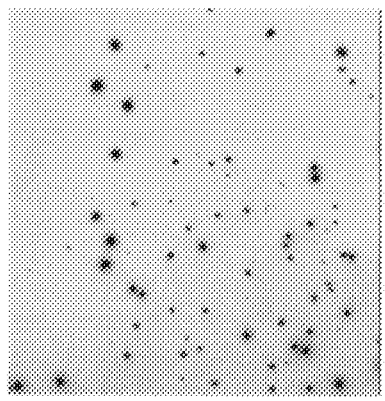
FIG. 2B shows colors and distribution of colonies containing amplified DNA from an individual with a premature stop codon in APC at position 4015. This sample is represented numerically in Table 1 with the samples in FIG. 2A and FIG. 2C.
Figure 2C:
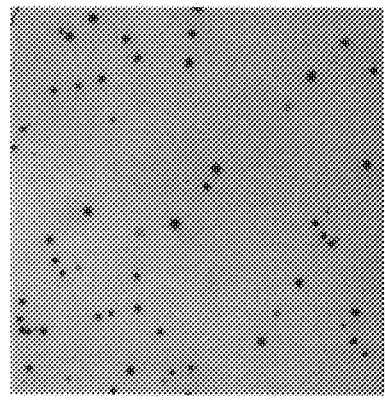
FIG. 2C shows colors and distribution of colonies containing amplified DNA from an individual with a colorectal carcinoma cell line (SW480) that is homo- or hemizygous for an APC stop mutation at position 4017. This sample is represented numerically in Table 1 with the samples in FIG. 2A and FIG. 2B.

The five DNAs used for this assay had been characterized previously using other methods of mutation detection. Each DNA sample was taken from an individual or tumor cell line with a different APC genotype: apc⁺/apc⁺, apc^m/apc⁺ and apc^m/apc^m (or apc^m/apc⁻). All five carried unique APC mutations within the region of the gene amplified by the primers. Each of these five different germline or tumor cell line APC mutations was detected with the assay of the present invention. Table 1 summarizes the results. The colony colors and their ratios for three samples are shown in FIG. 2 (A, B and C). DNA sequencing of colonies derived from several of these assays gave the expected sequences in every case.

B. Plasmid Construct and Preparation

The pSTDTAC-IKS plasmid is a 7.3 kb plasmid derived from pBR322 that contains the entire lacZ coding sequence.

A 300 bp insert containing multiple in-frame stops is flanked by ApaI and HindIII cleavage sites. This insertion is located between expression control sequences that include a Tac promoter, lac operator and translational start sequences, and the β-galactosidase coding sequence; in frame replacement of this out-of-frame insert is required for high levels of expression of the lacz gene. The plasmid also carries an ampicillin-resistance gene. Plasmid DNA was used to transform host bacterial strain XL1-Blue (Stratagene), which was grown in Terrific Broth and was isolated by means of a Qiagen Plasmid Preparation Column. The vector was cut with HindIII and ApaI restriction endonucleases (Boehringer Mannheim) and was gel-purified using Geneclean™.

C. Amplification of Test DNA and Cloning

Template DNA was obtained from APC patients, normal individuals, and colorectal carcinoma cell line SW480 (available from ATCC). APC mutations in DNAs had already been identified by other methods. (3, 10, 11). Insert DNA was prepared using the polymerase chain reaction (PCR) with the following pair of oligonucleotide primers: BWL2: GGCTGCAGGAATT CGATATCAAGCTTTGCT-GCCCATACACATTCAAACAC (SEQ ID NO: 1) and BWR4: GGCT GCGGAATTCGATATGGGCCCAT-GAGTGGGGTCTCCTGAAC (SEQ ID NO: 2). These primers amplify 1370 base pairs of APC sequence from nucleotide 2779 to 4151 in exon 15 of the APC gene, and include appropriate restriction sites for directional cloning into pSTDTAQ-IKS as well as nucleotides within BWL2 to adjust the frame of the DNA sequence produced. (There are no known ApaI or HindIII restriction sites in this segment of the APC gene.) DNA samples were amplified by the PCR: 5 min at 95° C., once; 1 min at 95° C., 1 min at 60° C., 1 min at 72° C., 30 cycles. Reaction mixtures contained the following: 200–400 ng of DNA template, 10 μM each primer, 75 μM each dNTP, 10 mM Tris pH 8.3, 50 mM KCl, 1.5 mM MgCl$_2$, 0.01% gelatin, 2.5 U of Taq polymerase. For each DNA sample analyzed, six PCR reactions were performed. Aliquots of each of these six PCR reactions were electrophoresed through a 2% ME agarose gel to check for amplification. The PCR products were pooled and split into two samples, which were each phenol/chloroform-extracted and ethanol-precipitated. Each pellet was washed once with 70% ethanol and resuspended in 20 μl of water. PCR products were digested sequentially with ApaI and HindIII. Enzymes were heat-inactivated at 65° C. for 20 min. Digested products were purified with Centricon 100 columns (Amicon) and electrophoresed to estimate DNA concentration. Products were mixed at a molar ratio of 1:2 or 1:3 (vector to insert) in a 20 μl ligation reaction using a Stratagene ligation kit.

D. Transformation and Plating

Cloned DNAs (1 μl of each of the 20 μl ligation reactions, or about 30 ng of vector DNA) were introduced into Sure™ Electrocompetent Cells (40 μl) (Stratagene) by electroporation in Bio-Rad Gene Pulser cuvettes. The transformation efficiency of these cells was approximately 5×10$^9$, as determined by the use pUC18 as a control. The electroporated cells were resuspended in 960 μl of S.O.C. medium (Bethesda Research Laboratories). Aliquots of 250 μl were then plated on each of two LB agar plates (180 cm) with 100 μg/ml ampicillin, 15 ug/ml tetracycline, and 80 μug/ml X-gal. IPTG was not included in the plating as the levels of constituitive expression were adequate for colorimetric determination and high expression levels appeared to inhibit colony formation. Plates were incubated overnight at 37° C. and stored at 4° C. to enhance the color of the colonies. Colony color and numbers were then scored, two days and again four days after incubation.

Alternatively, cloned DNAs, especially DNA amplified from clinical samples such as tumor tissue or stool samples, were introduced into galE$^-$, lacZ$^{31}$ E. coli cells as follows. The cells are grown in the presence of 0.1% phenylgalactoside to mid-log phase for preparation for CaCl$_2$ treatment for classical transformation or HEPES (1 mM, pH 7.0) treatment for electroporation. After transformation or electro-poration, the cells are allowed to express in LB medium supplemented with 0–0.5% phenyl-galactoside (25° C. for 2–4 hours or 37° C. for 30–60 minutes). The cells are then plated on selective LB agar medium containing 100 μg/ml ampicillin, 0–0.5% phenylgalactoside and 0.2% galactose. The concentration of phenylgalactoside is varied to modulate the ratio of killing of cells transformed with wild-type APC inserts (dark blue inserts) to survival of cells transformed with "chain-terminating" inserts (pale blue colonies).

E. Mutation Detection and DNA Sequencing

Colonies to be checked for the sequence of insert DNA were picked from the plates into 100 μl of water and boiled for 10 min. An aliquot was then PCR-amplified with custom APC primers (also carrying M13 universal or reverse sequencing primers) flanking the known mutation or with primers that were allele-specific for either of the two common APC deletions. Samples for sequencing were purified with Centricon-100 columns (Amicon) and finally sequenced with an Applied Biosystems model 373A DNA sequencer, as previously described.

Example 2

Screening the APC Gene

The five DNAs used for this assay had been characterized previously using other methods of mutation detection. Each DNA sample was taken from an individual or tumor cell line with a different APC genotype: apc$^+$/apc$^+$, apc$^m$/apc$^+$ and apc$^m$/apc$^m$ (or apc$^m$/apc$^m$). All five carried unique APC mutations within the region of the gene amplified by the primers.

Three types of bacterial colonies were seen with the assay using Sure™ described in Example 1. An intense blue colony was produced from in-frame cloning and maintenance of the reading frame in DNA that has a normal APC sequence. The intense blue colony resulted from the production of high levels of functional β-galactosidase protein. A white colony was produced by plasmid not carrying a cloned DNA insert, resulting in almost no production of β-galactosidase. The in-frame cloning of an insert that contained a sequence with a frameshift or a premature stop codon, however, produced a colony of intermediate blue color whose intensity varied with the specific mutation. The variable intensity may be due to reinitiation at downstream in-frame ATGs in the cloned APC segment (positions 2845, 2935, 3631 and 4150) or to factors specific to the plasmid and bacterial strains used in this assay.

The intermediate blue colonies derived from two types of inserts: mutations present in the original template DNA and errors generated by PCR amplification of the insert. This conclusion was supported by sequencing of dark and intermediate blue colonies derived from the testing of APC patient 3400. Each of three intermediate blue colonies sequenced contained the stop mutation found in this patient and each of three dark blue colonies contained normal APC sequence. However, four percent of colonies derived from DNA of a normal subject also were intermediate blue, implying that mutations were also present in these inserts, most likely generated by PCR.

Each of these five different germline or tumor cell line APC mutations was detected with the assay of the present invention. Table 1 summarizes the results showing colony colors and numbers obtained by cloning APC segments from different templates into the reporter plasmid and scoring for most samples was done at two and four days; both numbers are included below with the two day count to the left of the / and the four day number shown on the right. The colony colors and their ratios for three samples are shown in FIG. 2 (A, B and C). DNA sequencing of colonies derived from several of these assays gave the expected sequences in every case.

Figure 4:
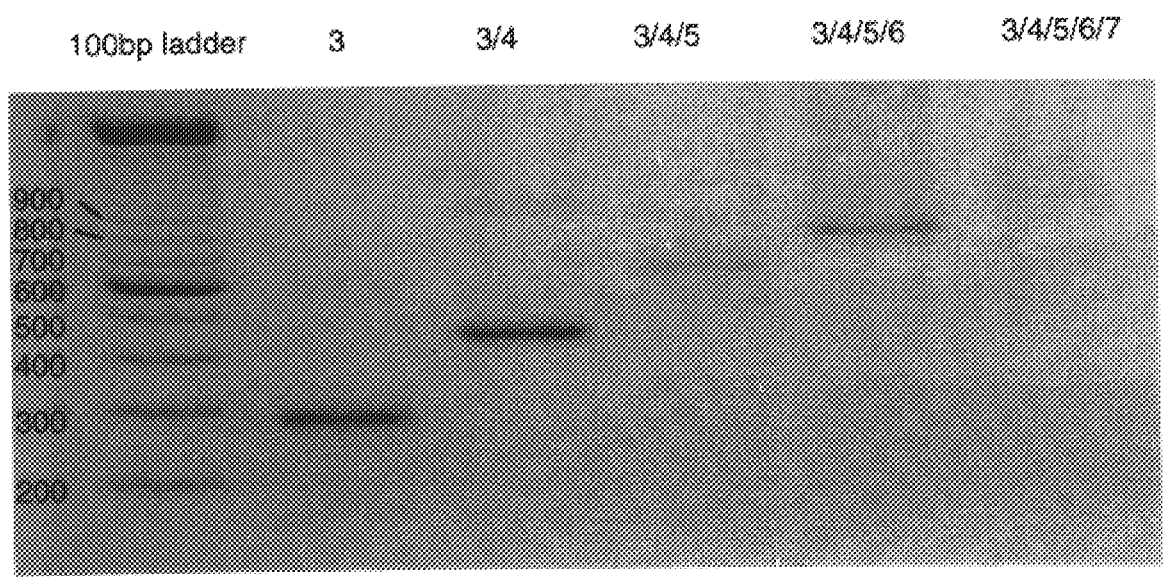
FIG. 4 shows the concantenation of exon 3 to exons 4, 5, 6 and 7. The reaction concentrations were as shown in FIGS. 3A and 3B with the exception that the templates were the reaction products shown in those figures and only the outside primers were added to each concatenation reaction.

Concantenation of exon 3 to exons 4, 5, 6 and 7 (lexon amplification) was successfully performed as shown in FIG. 4. Reaction concentrations were as described for the amplification of the individual exons with the exception that the templates were the products of the reactions shown in FIGS. 3A and 3B, and only the outside primers were added to each concantenation reaction. The secondary (concantenation)

TABLE 1

Colony Colors and Numbers Obtained by Cloning APC Segments form Different Templates into the Reporter Plasmid

| SAMPLE NAME | APC GENOTYPE | POSITION OF APC MUTATION | NUMBER OF BLUE COLONIES | NUMBER OF WHITE COLONIES | NUMBER OF LIGHT BLUE COLONIES |
|---|---|---|---|---|---|
| 97* | apc+/apc+ | — | 388 | 18 | 16 |
| 2379 | apc+/apc+ | — | 91/91 | 10/3 | 3/10 |
| 3400* | apc$^m$/apc+ | 4015 | 188 | 25 | 257 |
| 3400 | apc$^m$/apc+ | 4015 | 74/74 | 23/10 | 108/121 |
| 12046 | apc$^m$/apc+ | 3183 | 33/33 | 20/16 | 44/48 |
| 3493 | apc$^m$/apc+ | 3926 | 64/64 | 16/7 | 73/82 |
| 3794 | apc$^m$/apc+ | 2805 | 76 | 2 | 94 |
| SW480* | apc$^m$/apc$^m$ or apc$^m$/– | 4017 | 4 | 14 | 332 |
| SW480 | apc$^m$/apc$^m$ or apc$^m$/– | 4017 | 3/3 | 19/7 | 224/236 |

*Indicates that the DNA ligation was set up in a 1:2 vector-to-insert ratio. Scoring for most samples was done at two and four days; both numbers are included below with the two day count to the left of the / and the four day number shown on the right.

Example 3

Lexon Amplification of APC Gene

PCR amplification of exons 3, 4, 5, 6, 7, 8 and 9 is shown in FIGS. 3A and 3B. The amplification conditions for FIG. 3A were 10 mM Tris-HCl, 50 mM KCl, 1.5 mM MgCl$_2$, pH 8.3 at 20° C. The amplification conditions for FIG. 3B were the same except 4.5 mM MgCl$_2$ was used. All reactions had 1 μM of each primer, 125 nM dNTPs and 3% DMSO. The annealing temperatures and number of cycles were optimized for each exon in accordance with conventional practice. The observed size of each amplified exon was in agreement with the expected size for each product. Genomic template was used for the ampification of exons 3, 4, 5, 6 and 9. Exons 7 and 8 were most successfully amplified form a primary PCR using outside primers. Each of these products supported exon concantenation under various conditions as shown in FIG. 4.

PCRs were performed using a Hybaid "Omnigene" thermocycler (Labnet National Company, New Jersey) and the following generic cycling profile: 94° C. for 2 min., five cycles of (94° C. for 45 sec., 45° C. for 45 sec., 72° C. for 2 min.) and 30 cycles of (94° C. for 45 sec., 48° C. for 45 sec., 72° C. for 2 min.). The primers used for the concantenation reactions are shown in Table 2.

Linkage of exons 3 through 6 was relatively efficient compared with linkage of exons 3 through 7. Linkage of exons 8 and 9 was also relatively efficient. Linkage of exons 7 and 8 (data not shown in FIG. 4) is possible but very inefficient. As the order of exons in the concantenation unit does not effect the assay, concantenation in the order of exons 8, 9, 3, 4, 5, 6 and 7 is used for the screening method described herein. Table 3 shows the expected sizes of the various species produced in the concantenation reaction.

TABLE 2

Primers for Concantenation Reactions

| Primer Name | SEQ ID NO: | Sequence |
|---|---|---|
| 5Nco3Tm | 3 | TGCCCATGGTTGTTGTATAAAAACTTGTTTCTATTTTATTTAG |
| 5-34L | 4 | ATGGGAAACATTGCCGTCCCTTTTTTAAAAAAAAAAAAATAGGTCATT |
| 3-34L | 5 | TTTAAAAAAAGGGACGGCAATGTTTCCCATATGAAGAAAAGTTCCCTC |
| 5-45L | 6 | GTACAACTTATTTGGTTGATACTTTTTTATTATTTGTGGTTTAAG |
| 3-45L | 7 | ATAAAAAAGTATCAACCAAATAAGTTGTACTGCC44AAGTTACTTAC |
| 5-56L | 8 | CTAAGTGATAAAACAAAACTAATTAGGTTTCTTGTTTTATTTAAG |
| 3-56L | 9 | AAACCTAATTAGTTTTGTTTTATCACTTAGAAACAAGTAACTTAC |
| 5-67L | 10 | TTTTTGTTTGTGGGTCATGTACTGATGTTAACTCCATCTAAACAG |
| 3-67L | 11 | TAACATCAGTACATGACCCACAAACAAAAAAGGGAATTTACTAAC |
| 5-78L | 12 | TATCATATTTTTCCACGGACCATCTATAATGTGCTTAATTTTCAG |
| 3-78L | 13 | ATTATAGATGGTCCGTGGAAAAATATGATAAAATAATTTATTTAC |
| 5-89L | 14 | CAAACCCTGGTCACTATTTTGTTTCTAAACTCATTTGGCCCACAG |
| 3-89L | 15 | GTTTAGAAACAAAATAGTGACCAGGGTTTGTAATCTTCTGTTGAC |
| ApaInex9A | 16 | TACGGGGCCCATGTACACTATAGAGAACATAC |

TABLE 3

Expected Sizes for Concantentation Reactions

| Exon Number | 5' Primer | 3' Primer | Intron | Size 5' Primer | 3' Primer | Net | Concat'n 5'3' | Concat'n 3'5' |
|---|---|---|---|---|---|---|---|---|
| 3 | 5Nco3Tm | 3-34L | 202 | 48 | 48 | 293 | 293 | 1521 |
| 4 | 5-34L | 3-45L | 109 | 48 | 45 | 202 | 465 | 1258 |
| 5 | 5-45L | 3-56L | 111 | 45 | 45 | 201 | 636 | 1086 |
| 6 | 5-56L | 3-67L | 84 | 45 | 45 | 174 | 780 | 915 |
| 7 | 5-67L | 3-78L | 105 | 45 | 45 | 195 | 945 | 771 |
| 8 | 5-78L | 3-89L | 90 | 45 | 45 | 180 | 1095 | 606 |
| 9 | 5-89L | ApaInex9A | 379 | 45 | 32 | 456 | 1521 | 456 |

Industrial Utility

The present invention relates to a functional screen assay for nonsense and frameshift mutations that allows genes of interest to be scanned rapidly. The present invention provides an assay for the rapid screening for a number of genetic diseases, which are associated with nonsense and frameshift mutations. Such diseases include APC and retinoblastoma. In APC, for example, mutations result in a dramatic predisposition to gastrointestinal cancers. These mutations also result in the appearance of other benign and malignant neoplasia and minor developmental anomalies. This invention will improve the ability of researchers and clinical laboratories to detect chain-terminating mutations in APC and other genetic diseases. Therefore, this invention will improve the diagnostic and genetic services available to families and their at-risk children.

It will be appreciated that the methods and compositions of the instant invention can be incorporated in the form of a variety of embodiments, only a few of which are disclosed herein. It will be apparent to one skilled in the art that other embodiments exist and do not depart from the invention described herein. Thus, the described embodiments are illustrative and should not be construed as restrictive.

REFERENCES

1. Burt R. W. and Groden J. (1993). The genetic and molecular diagnosis of adenomatous polyposis coli. *Gastroent.* 104:949–952.
2. Nishisho, I., et al. (1991). Mutations of chromosome 5q21 genes in FAP and colorectal cancer patients. *Science* 253:665–669.
3. Powell, S. M., et al. (1992). APC mutations occur early during colorectal tumorigenesis. *Nature* 359:235–237.
4. Miyoshi, Y., et al. (1992). Somatic mutations of the APC gene in colorectal tumors: mutation cluster region in the APC gene. *Hum. Mol Genet.* 1:229–233.
5. Ichii, S., et al. (1992). Inactivation of both APC alleles in an early stage of colon adenomas in a patient with familial adenomatous polyposis (FAP). *Hum. Mol Genet.* 1:387–390.
6. Frebourg, T., et al. (1992). A functional screen for germ line p53 mutations based on transcriptional activation. *Can. Res.* 52:6976–6978.
7. Harris, C. (1993). p53: At the Crossroads of Molecular Carcinogenesis and Risk Assessment. *Science* 262:1980–1981.
8. U.S. Pat. No. 4,683,195; U.S. Pat. No. 4,613,202; Innis et al. (1990), PCR Protocols: A Guide to Methods and Applications, Academic Press, San Diego.
9. Wu et al. (1990). *Genomics* 4:560–569.
10. Groden, J., et al. (1991). Identification and characterization of the familial adenomatous polyposis coli gene. *Cell* 66:589–600.
11. Groden, J., et al. (1993). Mutational analysis of patients with adenomatous polyposis: identical inactivating mutations in unrelated individuals. *Am. J. Hum. Genet.* 52:263–272.

What is claimed is:

1. A method for detecting nonsense and frameshift mutations in a gene of interest or a portion thereof comprising:

(a) amplifying a first DNA sequence comprising the gene of interest or a portion thereof;

(b) combining said first DNA sequence upstream and in-frame with a second DNA sequence for a marker to produce a first fusion DNA;

(c) amplifying a third DNA sequence wherein said third DNA sequence is a known wild-type version of said first DNA sequence;

(d) combining said third DNA sequence upstream and in-frame with said second DNA sequence for a marker to produce a second fusion DNA;

(e) transforming bacterial cells with said first fusion DNA to produce a first set of transformed cells;

(f) transforming bacterial cells with said second fusion DNA to produce a second set of transformed cells;

(g) transforming bacterial cells with said second DNA sequence for a marker, wherein said marker yields only a background expression level in the absence of said first DNA or said third DNA, to produce a third set of transformed cells;

(h) growing said first set of transformed cells to allow expression of said first fusion DNA;

(i) growing said second set of transformed cells to allow expression of said second fusion DNA;

(j) growing said third set of transformed cells to determine a background expression level of said marker in the absence of said first DNA sequence and said third DNA sequence;

(k) detecting the level of expression of said marker in thirty or more colonies from said first set of transformed cells;

(l) detecting the level of expression of said marker in thirty or more colonies from said second set of transformed cells;

(m) detecting the level of expression of said marker in thirty or more colonies from said third set of transformed cells;

(n) comparing the level of expression of said marker obtained from said first set of transformed cells with the level of expression of said marker obtained from said third set of transformed cells (a negative control); and (o) comparing the level of expression of said marker obtained from said first set of transformed cells with the level of expression of said marker obtained from said second set of transformed cells (a positive control), wherein when 45% or more of colonies from said first set of transformed cells have a level of expression of said marker which is intermediate between the levels of expression of the negative control and the positive control, the gene of interest is determined to contain a nonsense or frameshift mutation.

2. The method of claim 1 wherein said first DNA sequence is amplified using a technique selected from group consisting of a polymerase chain reaction, a ligase chain reaction and a lexon creating reaction.

3. The method of claim 1 wherein the detection of said marker is accomplished using an immunological method, a spectrophotometric method or visual inspection.

4. The method of claim 3 wherein said immunological method is ELISA.

5. The method of claim 1 wherein said marker is β-galactosidase.

6. The method of claim 1 wherein said first DNA sequence comprises at least one exon of the adenomatous polyposis coli gene.

7. A method for detecting nonsense and frameshift mutations in a gene of interest or a portion thereof comprising:

(a) amplifying a first DNA sequence comprising the gene of interest or a portion thereof;

(b) combining said first DNA sequence upstream and in-frame with a second DNA sequence for a marker, wherein said second DNA codes for an enzyme, to produce a first fusion DNA;

(c) amplifying a third DNA sequence wherein said third DNA sequence is a known wild-type version of said first DNA sequence;

(d) combining said third DNA sequence upstream and in-frame with said second DNA sequence for a marker to produce a second fusion DNA;

(e) transforming bacterial cells with said first fusion DNA to produce a first set of transformed cells;

(f) transforming bacterial cells with said second fusion DNA to produce a second set of transformed cells;

(g) transforming bacterial cells with said second DNA sequence for a marker, wherein said marker yields only a background expression level of said enzyme in the absence of said first DNA or said third DNA, to produce a third set of transformed cells;

(h) growing said first set of transformed cells to allow expression of said first fusion DNA;

(i) growing said second set of transformed cells to allow expression of said second fusion DNA;

(j) growing said third set of transformed cells to determine a background expression level of said enzyme in the absence of said first DNA sequence and said third DNA sequence;

(k) detecting the level of expression of said enzyme in thirty or more colonies from said first set of transformed cells;

(l) detecting the level of expression of said enzyme in thirty or more colonies from said second set of transformed cells;

(m) detecting the level of expression of said enzyme in thirty five or more colonies from said third set of transformed cells;

(n) comparing the level of expression of said enzyme obtained from said first set of transformed cells with the level of expression of said enzyme obtained from said third set of transformed cells (a negative control); and (o) comparing the level of expression of said enzyme obtained from said first set of transformed cells with the level of expression of said enzyme obtained from said second set of transformed cells (a positive control), wherein when 45% or more of said colonies from said first set of transformed cells have a level of expression of said enzyme which is intermediate between the levels of expression of the negative control and the positive control, the gene of interest is determined to contain a nonsense or frameshift mutation.

8. The method of claim 7 wherein said first DNA sequence is amplified using a technique selected from group consisting of a polymerase chain reaction, a ligase chain reaction and a lexon creating reaction.

9. The method of claim 8 wherein said enzyme catalyzes a reaction forming a chromogenic or fluorogenic product.

10. The method of claim 9 wherein the detection of said enzyme is accomplished using a spectrophotometric method or visual inspection.

11. The method of claim 9 wherein said marker is β-galactosidase.

12. The method of claim 9 wherein said first DNA sequence comprises at least one exon of the adenomatous polyposis *coli* gene.

13. A method for detecting nonsense and frameshift mutations in a gene of interest or a portion thereof comprising:

(a) amplifying a first DNA sequence comprising the gene of interest or a portion thereof;

(b) combining said first DNA sequence upstream and in-frame with a second DNA sequence for a marker, wherein said second DNA codes for an epitope, to produce a first fusion DNA;

(c) amplifying a third DNA sequence wherein said third DNA sequence is a known wild-type version of said first DNA sequence;

(d) combining said third DNA sequence upstream and in-frame with said second DNA sequence for a marker to produce a second fusion DNA;

(e) transforming bacterial cells with said first fusion DNA to produce a first set of transformed cells;

(f) transforming bacterial cells with said second fusion DNA to produce a second set of transformed cells;

(g) transforming bacterial cells with said second DNA sequence for a marker, wherein said marker yields only a background expression level of said epitope in the absence of said first DNA or said third DNA, to produce a third set of transformed cells;

(h) growing said first set of transformed cells to allow expression of said first fusion DNA;

(i) growing said second set of transformed cells to allow expression of said second fusion DNA;

(j) growing said third set of transformed cells to determine a background expression level of said epitope in the absence of said first DNA sequence and said third DNA sequence;

(k) detecting the level of expression of said epitope in thirty or more colonies from said first set of transformed cells;

(l) detecting the level of expression of said epitope in thirty or more colonies from said second set of transformed cells;

(m) detecting the level of expression of said epitope in thirty or more colonies from said third set of transformed cells;

(n) comparing the level of expression of said epitope obtained from said first set of transformed cells with the level of expression of said epitope obtained from said third set of transformed cells (a negative control); and (o) comparing the level of expression of said epitope obtained from said first set of transformed cells with the level of expression of said epitope obtained from said second set of transformed cells (a positive control), wherein when 45% or more of said colonies from said first set of transformed cells have a level of expression of said epitope which is intermediate between the levels of expression of the negative control and the positive control, the gene of interest is determined to contain a nonsense or frameshift mutation.

14. The method of claim 13 wherein the detection of said first DNA sequence is amplified using a technique selected from group consisting of a polymerase chain reaction, a ligase chain reaction and a lexon creating reaction.

15. The method of claim 14 wherein the detection of said epitope is by ELISA.

16. The method of claim 14 wherein said first DNA sequence comprises at least one exon of the adenomatous polyposis *coli* gene.

17. The method of claim 7 wherein said enzyme catalyzes a reaction forming a chromogenic or fluorogenic product.

18. A method for detecting nonsense and frameshift mutations in a gene of interest or a portion thereof comprising:

(a) amplifying a first DNA sequence comprising the gene of interest or a portion thereof;

(b) combining said first DNA sequence upstream and in-frame with a second DNA sequence for a marker to produce a first fusion DNA;

(c) amplifying a third DNA sequence wherein said third DNA sequence is a known wild-type version of said first DNA sequence;

(d) combining said third DNA sequence upstream and in-frame with said second DNA sequence for a marker to produce a second fusion DNA;

(e) transforming bacterial cells with said first fusion DNA to produce a first set of transformed cells, wherein said bacterial cells contain a suppressor gene allowing readthrough of stop codons;

(f) transforming bacterial cells with said second fusion DNA to produce a second set of transformed cells, wherein said bacterial cells contain a suppressor gene allowing readthrough of stop codons;

(g) transforming bacterial cells with said second DNA sequence for a marker, wherein said marker yields only a background expression level of said marker in the absence of said first DNA or said third DNA, to produce a third set of transformed cells, wherein said bacterial cells contain a suppressor gene allowing readthrough of stop codons;

(h) growing said first set of transformed cells to allow expression of said first fusion DNA;

(i) growing said second set of transformed cells to allow expression of said second fusion DNA;

(j) growing said third set of transformed cells to determine a background expression level of said marker in the absence of said first DNA sequence and said third DNA sequence;

(k) detecting the level of expression of said marker in thirty or more colonies from said first set of transformed cells;

(l) detecting the level of expression of said marker in thirty or more colonies from said second set of transformed cells;

(m) detecting the level of expression of said marker in thirty or more colonies from said third set of transformed cells;

(n) comparing the level of expression of said marker obtained from said first set of transformed cells with the level of expression of said marker obtained from said third set of transformed cells (a negative control); and (o) comparing the level of expression of said marker obtained from said first set of transformed cells with the level of expression of said marker obtained from said second set of transformed cells (a positive control), wherein when 45% or more of said colonies from said first set of transformed cells have a level of expression of said marker which is intermediate between the levels of expression of the negative control and the positive control, the gene of interest is determined to contain a nonsense or frameshift mutation.

19. The method of claim 18 wherein said first DNA sequence is amplified using a technique selected from a group consisting of a polymerase chain reaction, a ligase chain reaction and a lexon creating reaction.

20. The method of claim 18 wherein the detection of said marker is accomplished using an immunological method, a spectrophotometric method or visual inspection.

21. The method of claim 20 wherein said immunological method is ELISA.

22. The method of claim 18 wherein said marker is β-galactosidase.

23. The method of claim 18 wherein said first DNA sequence comprises at least one exon of the adenomatous polyposis *coli* gene.

24. A method for detecting nonsense and frameshift mutations in a gene of interest or a portion thereof comprising:

(a) amplifying a first DNA sequence comprising the gene of interest or a portion thereof;

(b) combining said first DNA sequence upstream and in-frame with a second DNA sequence for a marker, wherein said second DNA codes for an enzyme, to produce a first fusion DNA;

(c) amplifying a third DNA sequence wherein said third DNA sequence is a known wild-type version of said first DNA sequence;

(d) combining said third DNA sequence upstream and in-frame with said second DNA sequence for a marker to produce a second fusion DNA;

(e) transforming bacterial cells with said first fusion DNA to produce a first set of transformed cells, wherein said bacterial cells contain a suppressor gene allowing readthrough of stop codons;

(f) transforming bacterial cells with said second fusion DNA to produce a second set of transformed cells, wherein said bacterial cells contain a suppressor gene allowing readthrough of stop codons;

(g) transforming bacterial cells with said second DNA sequence for a marker, wherein said marker yields only a background expression level of said enzyme in the absence of said first DNA or said third DNA, to produce a third set of transformed cells, wherein said bacterial cells contain a suppressor gene allowing readthrough of stop codons;

(h) growing said first set of transformed cells to allow expression of said first fusion DNA;

(i) growing said second set of transformed cells to allow expression of said second fusion DNA;

(j) growing said third set of transformed cells to determine a background expression level of said enzyme in the absence of said first DNA sequence and said third DNA sequence;

(k) detecting the level of expression of said enzyme in thirty or more colonies from said first set of transformed cells;

(l) detecting the level of expression of said enzyme in thirty or more colonies from said second set of transformed cells;

(m) detecting the level of expression of said enzyme in thirty or more colonies from said third set of transformed cells;

(n) comparing the level of expression of said enzyme obtained from said first set of transformed cells with the level of expression of said enzyme obtained from said third set of transformed cells (a negative control); and (o) comparing the level of expression of said enzyme obtained from said first set of transformed cells with the level of expression of said enzyme obtained from said second set of transformed cells (a positive control), wherein when 45% or more of said colonies from said first set of transformed cells have a level of expression of said enzyme which is intermediate between the levels of expression of the negative control and the positive control, the gene of interest is determined to contain a nonsense or frameshift mutation.

25. The method of claim 24 wherein said enzyme catalyzes a reaction forming a chromogenic or fluorogenic product.

26. The method of claim 24 wherein said first DNA sequence is amplified using a technique selected from a group consisting of a polymerase chain reaction, a ligase chain reaction and a lexon creating reaction.

27. The method of claim 26 wherein said enzyme catalyzes a reaction forming a chromogenic or fluorogenic product.

28. The method of claim 27 wherein the detection of said enzyme is accomplished using a spectrophotometric method or visual inspection.

29. The method of claim 27 wherein said marker is β-galactosidase.

30. The method of claim 27 wherein said first DNA sequence comprises at least one exon of the adenomatous polyposis *coli* gene.

31. A method for detecting nonsense and frameshift mutations in a gene of interest or a portion thereof comprising:

(a) amplifying a first DNA sequence comprising the gene of interest or a portion thereof;

(b) combining said first DNA sequence upstream and in-frame with a second DNA sequence for a marker, wherein said second DNA codes for an epitope, to produce a first fusion DNA;

(c) amplifying a third DNA sequence wherein said third DNA sequence is a known wild-type version of said first DNA sequence;

(d) combining said third DNA sequence upstream and in-frame with said second DNA sequence for a marker to produce a second fusion DNA;

(e) transforming bacterial cells with said first fusion DNA to produce a first set of transformed cells, wherein said bacterial cells contain a suppressor gene allowing readthrough of stop codons;

(f) transforming bacterial cells with said second fusion DNA to produce a second set of transformed cells, wherein said bacterial cells contain a suppressor gene allowing readthrough of stop codons;

(g) transforming bacterial cells with said second DNA sequence for a marker, wherein said marker yields only a background expression level of said epitope in the absence of said first DNA or said third DNA, to produce a third set of transformed cells, wherein said bacterial cells contain a suppressor gene allowing readthrough of stop codons;

(h) growing said first set of transformed cells to allow expression of said first fusion DNA;

(i) growing said second set of transformed cells to allow expression of said second fusion DNA;

(j) growing said third set of transformed cells to determine a background expression level of said epitope in the absence of said first DNA sequence and said third DNA sequence;

(k) detecting the level of expression of said epitope in thirty or more colonies from said first set of transformed cells;

(l) detecting the level of expression of said epitope in thirty or more colonies from said second set of transformed cells;

(m) detecting the level of expression of said epitope in thirty or more colonies from said third set of transformed cells;

(n) comparing the level of expression of said epitope obtained from said first set of transformed cells with the level of expression of said epitope obtained from said third set of transformed cells (a negative control); and (o) comparing the level of expression of said epitope obtained from said first set of transformed cells with the level of expression of said epitope obtained from said second set of transformed cells (a positive control), wherein when 45% or more of said colonies from said first set of transformed cells have a level of expression of said epitope which is intermediate between the levels of expression of the negative control and the positive control, the gene of interest is determined to contain a nonsense or frameshift mutation.

32. The method of claim 31 wherein the detection of said first DNA sequence is amplified using a technique selected from a group consisting of a polymerase chain reaction, a ligase chain reaction and a lexon creating reaction.

33. The method of claim 32 wherein the detection of said epitope is by ELISA.

34. The method of claim 32 wherein said first DNA sequence comprises at least one exon of the adenomatous polyposis *coli* gene.

* * * * *

UNITED STATES PATENT AND TRADEMARK OFFICE
CERTIFICATE OF CORRECTION

PATENT NO.    : 5,876,940
DATED         : March 2, 1999
INVENTOR(S)   : Joanna L. Groden, Raymond L. White, Lisa Spirio, Margaret Robertson,
                Robert Weiss, Therese Tuohy and Liliana Varesco It is certified that error appears in the above-identified patent and that said Letters Patent is hereby corrected as shown below:

<u>Title page,</u>
Item [75], Inventors, please change the paragraph of inventors to read:
-- Joanna L. Groden, Cincinnati, Ohio; Raymond L. White, Salt Lake City, Utah;
Lisa Spirio, Salt Lake City, Utah; Margaret Robertson, Salt Lake City, Utah;
Robert Weiss, Salt Lake City, Utah; Thèrèse Tuohy, Cincinnati, Ohio;
Liliana Varesco, Genova, Italy. --

Signed and Sealed this

Tenth Day of September, 2002

*Attest:*

*Attesting Officer*

JAMES E. ROGAN
*Director of the United States Patent and Trademark Office*